United States Patent
Granstrom et al.

(10) Patent No.: US 9,024,066 B2
(45) Date of Patent: May 5, 2015

(54) METHOD FOR RECOVERING AND PURIFYING PROPIONIC ACID

(71) Applicant: Taminco Finland, Oulu (FI)

(72) Inventors: Tom Granstrom, Rajamaki (FI); Juhana Ahola, Vantaa (FI); Jukka Hietala, Porvoo (FI); Esko Tirronen, Espoo (FI)

(73) Assignee: Taminco Finland, Oulu (FI)

( * ) Notice: Subject to any disclaimer, the term of this patent is extended or adjusted under 35 U.S.C. 154(b) by 0 days.

(21) Appl. No.: 14/361,436

(22) PCT Filed: Nov. 26, 2012

(86) PCT No.: PCT/FI2012/051166
§ 371 (c)(1),
(2) Date: May 29, 2014

(87) PCT Pub. No.: WO2013/079785
PCT Pub. Date: Jun. 6, 2013

(65) Prior Publication Data
US 2014/0330039 A1 Nov. 6, 2014

(30) Foreign Application Priority Data
Dec. 1, 2011 (FI) .................................... 20116209

(51) Int. Cl.
*C07B 41/08* (2006.01)
*C07C 51/42* (2006.01)
*C07C 51/44* (2006.01)
*C07C 51/48* (2006.01)
*C12P 7/52* (2006.01)

(52) U.S. Cl.
CPC ................. *C07C 51/42* (2013.01); *C07C 51/44* (2013.01); *C07C 51/48* (2013.01); *C12P 7/52* (2013.01)

(58) Field of Classification Search
CPC ................................ C07C 51/44; C07C 51/48
See application file for complete search history.

(56) References Cited

U.S. PATENT DOCUMENTS

| | | | | |
|---|---|---|---|---|
| 2,556,228 A * | 6/1951 | Souders, Jr. | .................. | 540/324 |
| 2011/0124913 A1 | 5/2011 | Dubois | | |
| 2011/0125118 A1* | 5/2011 | Lynch | ........................... | 604/367 |

FOREIGN PATENT DOCUMENTS

| | | |
|---|---|---|
| EP | 1 385 593 B1 | 8/2006 |
| GB | 689411 A | 3/1953 |
| WO | 02/074403 A1 | 9/2002 |
| WO | 2005/073161 A1 | 8/2005 |
| WO | 2009/154624 A1 | 12/2009 |

OTHER PUBLICATIONS

Lewis et al, Biotechnology Progress, A Novel Extractive Fermentation Process for Propionic Acid Production from Whey Lactose, 1992, pp. 104-110.*
Posada et al, Industrial & Engineering Chemical Research, Propionic Acid Production from Raw Glycerol Using Commercial and Engineered Strains, 2012, 51(5), pp. 2354-2361.*
Amit Keshav et al., "Recovery of propionic acid from an aqueous stream by reactive extraction: effect of diluents", Desalination 2009, pp. 12-23, vol. 244, No. 1-3.
Amit Keshav et al., "Reactive Extraction of Propionic Acid Using Tri-n-octylamine", Chem. Eng. Comm. 2010, pp. 606-626, vol. 197, No. 4.
Amit Keshav et al., "Effect of binary extractants and modifier-diluents systems on equilibria of propionic acid extraction", Fluid Phase Equilibria 2009, pp. 21-26, vol. 275, No. 1.
John A. Posada et al., "Propionic Acid Production from Raw Glycerol Using Commercial and Engineered Strains", Ind. & Eng. Chem. Res. 2012, pp. 2354-2361, vol. 51, No. 5.
Patrick Boyaval et al., "Propionic acid production in a membrane bioreactor", Enzyme Microb. Technol., Oct. 1994, pp. 883-886, vol. 16, No. 10.
Andre Bories et al., Glycerol Fermentation with Propionibacteria and optimisation of the production of propionic acid, Sciences des Ailments 2004, pp. 121-138, vol. 24, No. 2.
Finnish Search Report for FI 20116209 dated Aug. 9, 2012.
International Search Report for PCT/FI2012/051166 dated Apr. 3, 2013.
Written Opinion for PCT/FI2012/051166 dated Apr. 3, 2013.
Choi, Won J., "Glycerol-Based Biorefinery for Fuels and Chemicals," Recent Patents on Biotechnology, 2008, vol. 2, No. 3, pp. 173-180 (8 pages total).
Lewis et al., "A Novel Extractive Fermentation Process for Propionic Acid Production from Whey Lactose," Biotechnol Prog., 1992, vol. 8, No. 2, pp. 104-110 (7 pages total).
Zhang et al., "Propionic acid production from glycerol by metabolically engineered Propionibacterium acidipropionici," Process Biochemistry, 2009, vol. 44, pp. 1346-1351 (6 pages total).
Zhu et al., "Optimization and scale-up of propionic acid production by propionic acid-tolerant *Propionibacterium acidipropionici* with glycerol as the carbon source," Bioresource Technology, vol. 101, 2010, pp. 8902-8906 (5 pages total).

* cited by examiner

*Primary Examiner* — Paul A Zucker
(74) *Attorney, Agent, or Firm* — Sughrue Mion, PLLC

(57) ABSTRACT

The present invention provides a method for purifying and recovering propionic acid from an aqueous mixture containing a fermentation product obtained from a fermentation process using glycerol as substrate, the method comprising optionally acidifying the aqueous mixture to a pH below 4.5, subjecting the aqueous mixture to an extraction with extracting agent containing a heavy extractant and optionally a light extractant as a diluent to obtain an extract comprising the extracting agent and organic acids, and a raffinate comprising water and any unreacted glycerol, and subjecting the extract to vacuum evaporation to separate propionic acid-containing organic acids from the extractant.

23 Claims, 3 Drawing Sheets

METHOD FOR RECOVERING AND PURIFYING PROPIONIC ACID

CROSS REFERENCE TO RELATED APPLICATIONS

This application is a National Stage of International Application No. PCT/FI2012/051166 filed Nov. 26, 2012, claiming priority based on Finnish Patent Application No. 20116209 filed Dec. 1, 2011, the contents of all of which are incorporated herein by reference in their entirety.

FIELD OF THE INVENTION

The present invention relates to a method for recovering and purifying propionic acid from an aqueous mixture containing a fermentation product obtained from a fermentation process using glycerol as substrate.

BACKGROUND OF THE INVENTION

Propionic acid (also called propanoic acid) is a naturally occurring carboxylic acid with chemical formula $CH_3CH_2COOH$. It can be used as solvent, as food preservative or in the herbicide manufacture. Propionic acid is also useful as an intermediate in the production of other chemicals, especially polymers. Cellulose-acetate-propionate is a useful thermoplastic. Vinyl propionate is also used as monomer in (co)polymers with e.g. ethylene, vinyl chloride and (meth)acrylic esters. In more specialized applications it is also used to make pesticides and pharmaceuticals. The esters of propionic acid have fruit-like odors and are sometimes used as solvents or artificial flavorings.

Processes for the production of propionic acid are known in the art. Currently, almost all propionic acid is produced by chemical synthesis from petroleum feedstocks.

US 2011/0124913 discloses a process for the industrial manufacture of propionic acid from glycerol. This makes it possible to obtain a bioresourced propionic acid from renewable resources. In this complicated chemical process containing several energy consuming isolation steps, glycerol is first dehydrogenated to acrolein, acrolein is oxidized to acrylic acid and acrylic acid is finally hydrogenated to propionic acid.

The propionic acid could also be produced by propionibacteria via the dicarboxylic acid pathway with acetic acid and succinic acid as byproducts, but low yield and productivity due to the inhibition of propionic acid on cell growth and propionic acid synthesis is a problem. Like most organic acid fermentations, the propionic acid fermentation is inhibited by acidic pHs and the major fermentation product, propionic acid. Furthermore, the fermentation is heterogenous, i.e. propionate is produced along with other by-products. This not only results in a low product yield but also renders product purification difficult and expensive.

To alleviate the inhibition of propionic acid on microbial growth and propionic acid synthesis, two approaches, extractive propionic acid fermentation and propionic acid production with propionic acid-tolerant bacteria obtained via adaptive evolution have been developed. Despite such advancements, current microbial propionic acid production cannot economically compete with petrochemical routes. Producing propionic acid from agricultural and industrial wastes may make microbial propionic acid production economically competitive. Glycerol is a main by-product of the biodiesel industry and could thus be a low-cost feedstock to produce propionic acid. While most studies on propionic acid production by *Propionibacterium acidipropionici* have focused on glucose and whey lactose, some studies have explored glycerol as the carbon source, and it was observed that glycerol might be advantageous since less acetic acid was produced during the consumption of glycerol (Zhu et al. Optimization and scale-up of propionic acid production by propionic acid-tolerant *Propionibacterium acidipropionici* with glycerol as the carbon source, Bioresource Technology 101 (2010), 8902-8906).

The rapidly expanding market for bioethanol and biodiesel is remarkably altering the cost and availability of glycerol. In general, approximately 10 pounds of crude glycerol are formed for every 100 pounds of biodiesel produced. Bioethanol process also generates glycerol up to 10% (w/w) of the total sugar consumed as a byproduct. Crude glycerol has thus been widely recognized as an attractive sustainable resource for chemical industries. Glycerol-based biorefinery is the microbial fermentation process using inexpensive and readily available glycerol as the raw material to produce fuels and chemicals. A major challenge in fermentation of the low-grade crude glycerol is to obtain microbial strains tolerant to undesirable inhibitory components such as salts and organic solvents that present in crude glycerol. There have been several attempts to explore anaerobic microbial assimilation of glycerol using reconstructed microbial systems via microbial screening and metabolic pathway engineering. As a result, fuels as well as some high-value products were found to be produced by microbial fermentation of glycerol (Choi, W. J., Glycerol-Based Biorefinery for Fuels and Chemicals, Recent Pat Biotechnol. 2008; 2(3):173-80).

Glycerol (or glycerin) is the principal component of triglycerides and it is clear, odorless and viscous liquid. It is found in animal fats, vegetable oils or petrochemical feedstocks, and it is derived from soap or biodiesel production. Choi (2008, supra) describes microbial metabolic pathways of glycerol for fuels and chemicals, and different glycerol-based fermentative products, such as ethanol, biogas and organic acids.

Zhu et al. (2010, supra) describe propionic acid production by propionic acid-tolerant *Propionibacterium acidipropionici* with glycerol as sole carbon source in batch cultures and then scaled-up production in a 10 $m^3$ fermentor using the optimized conditions.

Zhang and Yang (Process Biochemistry 44 (2009) 1346-1351) describe a process for propionic acid production from glycerol by using metabolically engineered *Propionibacterium acidipropionici* in free-cell fermentation.

Boyaval, P. et al (Enzyme Microb Technol., 1994, vol. 16, 883-886) describe fermentation of glycerol by propionic acid bacteria to obtain propionic acid with no acetic acid. The method comprises subjecting the medium to ultrafiltration.

Extractive fermentation is generally a process for producing a variety of chemical products by fermentation in which the product is removed from the fermentation medium as it is formed by liquid-liquid extraction using an extractant which is immiscible with water.

Yang and Lewis (A Novel Extractive Fermentation Process for Propionic Acid Production from Whey Lactose, Biotechnol. Prog, 1992, 8, 104-110) describe an extractive fermentation process to produce propionate from lactose. Extractive fermentation removes the inhibitory acidic product from the reactor and therefore provides better pH control on the reactor and results in higher reaction rates. Alamine 336/2-octanol mixture was used as the extractant in an extractive fermentation process for propionate production from whey lactose. In lactose fermentation the main by-products are acetic acid and carbon dioxide.

There is a need for novel and efficient methods for purifying and recovering propionic acid from fermentations wherein glycerol is used as the starting material. The specific conditions, such as different by-products than in e.g. lactose fermentation, make it challenging.

BRIEF DESCRIPTION OF THE INVENTION

The present invention provides a method for purifying and recovering propionic acid from an aqueous mixture containing a fermentation product obtained from a fermentation process using glycerol as substrate, the method comprising
optionally acidifying the aqueous mixture to pH below 4.5,
subjecting the aqueous mixture to an extraction with extracting agent comprising a heavy extractant and optionally a light extractant as a diluent to obtain an extract containing the extracting agent and organic acids, and a raffinate containing water and any unreacted glycerol, and
subjecting the extract to vacuum evaporation to separate propionic acid-containing organic acids from the extractant.

It is an advantage of the present invention that very pure end-product is obtained. The method of the invention has superior resolving properties. All the components of the starting material may be separated. Especially when purifying propionic acid, no or very little evaporation of water is needed. Further, any remaining glycerol from the fermentation process may be easily recovered and recycled back to the fermentation. Also the extraction diluent may be recovered even in one step.

It is another advantage of the present invention that no filtration steps, such as ultrafiltration, are required in the separation of the propionic acid.

The present method containing extraction and distillation is superior compared to e.g. generally used CaO precipitation due to product purity. Conventional precipitation results mixtures of salts, such as Ca-propionate, Ca-acetate and Ca-succinate, which are difficult to separate.

It is another advantage of the present invention that pure propionic acid is recovered instead of salt thereof.

DETAILED DESCRIPTION OF THE INVENTION

Figure 1:
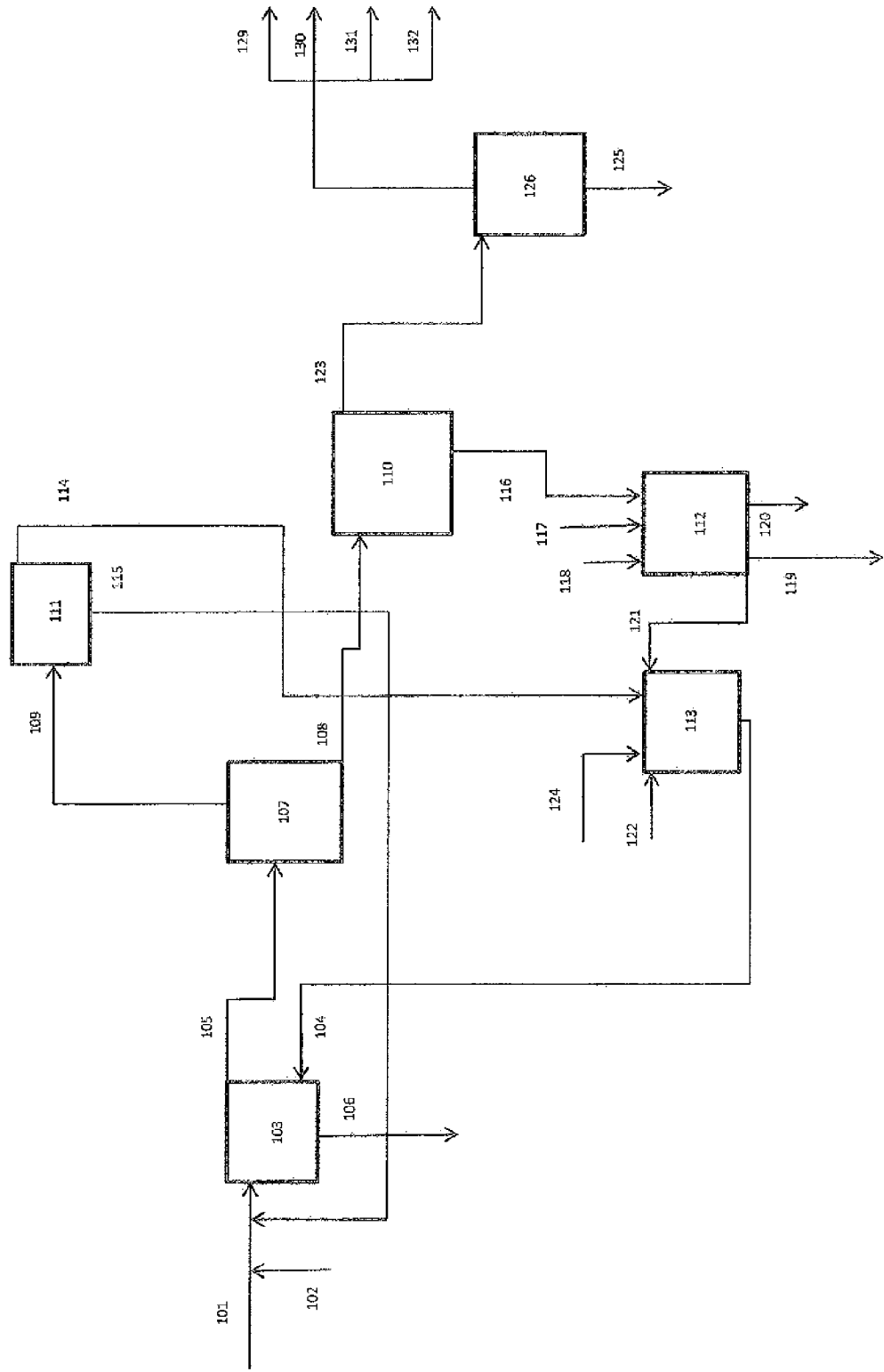
FIG. 1 shows a process flow chart of the downstream separating and recovering process from the aqueous feed to the end product(s).

The present inventors have developed a process for bio-based organic acid production, such as propionic acid, from crude glycerol. The process may be applied to organic acid production in a continuous immobilized cell column reactor, and product is recovered with optimized extraction and distillation processes.

The process can be used for various organic acid productions from different sugar-rich biomasses, but a preferable process is propionic acid production from crude glycerol, which may be derived for example from a FAME biodiesel production process. According to Zhang and Yang (supra), compared to glucose as the carbon source, both cell growth (0.05 $h^{-1}$ vs. 0.13 $h^{-1}$) and propionic acid productivity (0.026 g/l h vs. 0.22 g/l h) are significantly lower in glycerol fermentation although the propionic acid yield (0.55 g/g vs. 0.37 g/g) is significantly higher. Glycerol, as a more reduced substrate, would shift the metabolic pathway toward propionic acid production so cells could maintain redox balance. In addition, glycerol fermentation does not produce any carbon dioxide. Thus, glycerol is superior raw material for propionic acid production.

Crude glycerol contains typically 80% glycerol and by-products, such as organic matter and salts. In order to remove these by-products, a membrane can be installed before the feeding tank directly to crude glycerol line and/or to the raffinate water line from the downstream section.

In the described propionic acid production process, propionic acid is the main product with typical concentration of about 3% (w/w) in the fermentation broth. Succinic acid and acetic acid are typically formed as the main side products. The solution may contain also other organic compounds such as $C_4$-$C_6$ monoacids, propanol and non-reacted or remaining glycerol, which has not been used in the fermentation. Typically propionic acid productivity of the process is 1-5 g/h/l, when crude glycerol is used as the carbon source, and yeast extract as the nitrogen source. Other nutrients, such as phosphates and salts, are also optimized for cell growth and acid production. In one example the feeding flow contains 40-100 g/l glycerol, the dilution rate through the column bioreactor is adjusted, preferably to 0.1-0.01 1/l, the process pH is maintained around 6 by using an on-line NaOH feeding device, and the process temperature is maintained preferably at +32-37° C.

Propionic acid is recovered from the fermentation broth by using extraction and distillation phases. Several extraction chemicals may be used. The extraction may be done in a countercurrent column in order to increase the extraction efficiency. The acids can then be separated from the heavy reactive extractant by using distillation and/or alkaline wash. Depending on the distillation pressure and temperature, propionic acid and other light acids can be collected and further purified with additional distillations. Succinic acid may be removed from the heavy extractant by alkaline wash as a salt.

By using this process, bio-based propionic acid can be produced in an environmentally and economically feasible way and further, the formed propionic acid can be used either as such for biomass (e.g. feed) preservation, or as a raw material for propionates production, to be sold e.g. as a preservative for food industry. It is also possible to use the light acid fraction as such in some applications.

The present invention provides a method for purifying and recovering propionic acid from an aqueous mixture containing a fermentation product obtained from a fermentation process using glycerol as substrate. First the aqueous mixture may be acidified from about 6-6.5 to pH below 4.5 if necessary in order to convert carboxylic acid salts to free acids, which are then extracted from the aqueous phase to the organic phase.

Generally the fermentation broth or the aqueous mixture or solution containing the fermentation product contains sodium propionate, sodium acetate, mono- and disalts of sodium succinates, glycerol and water as the main components and it has pH of about 6, for example about 6.2.

In one embodiment the aqueous mixture is acidified to pH below 4.5 with an inorganic acid, such as sulfuric acid. In one embodiment the pH of the acidified aqueous mixture is acidified to pH of about 4. In one embodiment the pH of the acidified aqueous mixture is acidified to pH of about 3.5. After the acidification the aqueous solution contains the ingredients mainly in acid form, such as propionic acid, acetic acid, succinic acid, and $H_2SO_4$, (when acidified with $H_2SO_4$), and as inorganic salts. If NaOH is used in the pH control of fermentation and $H_2SO_4$ in the acidification, $Na_2SO_4$ is formed in this step.

Next, the aqueous mixture is subjected to an extraction with extracting agent comprising a heavy extractant and optionally a light extractant as a diluent to obtain an extract comprising the extracting agent and organic acids, and a raffinate comprising water and any unreacted glycerol. The term "raffinate" as used herein refers to the residual glycerol-containing aqueous phase after the extraction. There may be one or more extractions or extraction steps to increase the extraction selectivity to propionic acid, such as two, three or four steps.

In one embodiment the glycerol-containing raffinate from the extraction is recycled back to the fermentation process, such as to the fermentation broth. The glycerol from the raffinate may be concentrated by membrane filtration prior recycling back to the fermentation.

The term "extract" as used herein refers to the composition formed after extraction comprising the extracting agent(s) and the valuable compounds to be recovered, i.e. the organic acids. The terms "extractant" and "extracting solvent" as used herein generally refer to the extracting agent. Extracting agent may contain a heavy extractant and a light extractant wherein the heavy extractant generally contains the extracting agent itself and the optional light extractant contains a diluent or a solvent.

The extracting agent or extracting solvent may contain a heavy trialkyl amine with 15-36 carbons, such as trihexyl amine, trioctyl amine, triisooctylamine, trioctyl/decyl amine (such as Alamine 336) and tridodecylamine or a mixture thereof, as the heavy extractant, optionally combined with a hydrocarbon diluent with 6 or 7 carbons, such as n-hexane, n-heptane, cyclohexane, benzene or toluene or a mixture thereof as the light extractant. In one specific embodiment the extracting agent comprises tri-octyl/decyl amine with cyclohexane. The purpose of the diluent is to lower the viscosity of the extractant, facilitate the phase separation and carry light side products and impurities. The amount needed (if any) depends on the amine used and the concentration of the light component in the fermentation product. In one embodiment the extracting agent contains light extractant in the amount of 10-50% (w/w), preferably in the amount of 40-50% (w/w). In one embodiment the extracting agent comprises tri-octyl/decyl amine with cyclohexane, such as 40-50% (w/w) of cyclohexane, for example about 45% (w/w) of cyclohexane. The ratio (w/w) of the extracting agent to light extractant may be in the range of 80:20-30:70, such as in the range of 50:50-70:30, for example in the range of 60:40-70:30, such as about 67:33.

The extraction may be carried out at a temperature in the range of about 10-80° C., such as in the range of about 10-70° C., for example in the range of about 20-40° C. The extraction may be carried out at a pressure of 500 kPa, such as at a pressure of 300 kPa, for example at ambient pressure (about 100 kPa) wherein the pressure is not regulated.

In one embodiment the mass ratio of the dilute aqueous mixture to the extracting agent in the feed ("aqueous to organic feed") is in the range of 0.25-4.0, for example the range of 0.75-2.0. The ratio may also be expressed as "o/w" (organic/water) which is the ratio of extractant/feed (g/g).

In one embodiment the extraction is performed in a counter-current operating extraction column, such as in a continuously operating counter-current extraction column. The extraction column may comprise several chambers which may include mixing in each to ensure efficient contact between the components and more controlled concentration separations.

When the extraction is performed in a counter-current extraction column, the yield of propionic acid after the extraction is generally more than 60% (w/w) calculated from the extract (organic phase).

After the phase separation the obtained organic phase (the extract) generally contains the extractants, organic acids, such as propionic acid, acetic acid, succinic acid, etc.; and traces of glycerol and water. The obtained aqueous phase (the raffinate) generally contains water, glycerol, $Na_2SO_4$, and $H_2SO_4$, (when pH is regulated with NaOH and acidified with $H_2SO_4$).

Next, the extract is subjected to one or more vacuum distillations or evaporations to separate propionic acid-containing light organic acids, especially the propionic acid, from the heavy extractant containing heavy organic acids such as succinic acid. The vacuum evaporation step may also be called stripping, such as a stripping distillation, which as used herein generally refers to a separation of extracted compounds from the organic extractants. In one embodiment the extractant from vacuum evaporation is recycled and washed back to the extraction. The heavy organic acids, such as succinic acid, may be recovered as salts by washing the heavy extractant with alkaline aqueous solution. In one embodiment the extract is subjected to one or more vacuum distillations or evaporations directly from the extraction i.e. there is no additional steps in between.

Removal of the light organic acids, such as propionic acid and acetic acid from heavy extraction agents by vacuum evaporation is carried out at a temperature in the range of 30-200° C., such as in the range of 50-180° C., for example in the range of 60-170° C. In one embodiment the vacuum evaporation is carried out at a pressure below 25 kPa, for example below 10 kPa.

In one example the top stream of the vacuum evaporation comprising light organic acids, for example acetic acid and propionic acid, comprises water less than 5% by weight.

The process may contain also other steps, such as co-solvent distillation if a solvent is present in the extraction, and one or more acid distillations to further purify the end product.

Before the vacuum evaporation the extract containing the organic acids may be subjected to co-solvent distillation to obtain a distillate, which is drawn from top part of a distillation column, containing light extractant solvent and some water, and a bottom stream containing essentially the organic acids (e.g. propionic acid, acetic acid, succinic acid) and the heavy extractant.

Therefore, in one embodiment the method further comprises subjecting the extract from the extraction to co-solvent distillation to separate a co-solvent fraction containing any light extractant, light side products and water, from the extract containing the heavy extractant, organic acids and any impurities. In one embodiment the method comprises, generally after separation of light extractant and water in the distillate, recycling the light extractant back to the extraction, more precisely back to the extractant preparation, and/or recycling water back to the extraction column. In another embodiment the method is carried out without co-solvent distillation, or other purification or isolation steps between the extraction and vacuum evaporation.

Removal of the light extraction agents from the extract by said distillation may be carried out at a temperature in the range of 30-110° C., preferably in the range of 35-105° C., and most preferably in the range of 35-85° C., such as at about 35-45° C. In one embodiment the distillation is carried out at pressure down to typically 25 kPa, when distilling the cyclohexane and water. Said distillation temperature refers to the temperature at the top part of the distillation column.

In one example the bottom stream of the distillation column comprising the heavy extractant and the organic acids (e.g. propionic acid, acetic acid and succinic acid) comprises water less than 5% by weight and less than 0.2% of the light extracting agent, such as cyclohexane.

Finally, the organic acids from the vacuum evaporation may be subjected to one or more acid distillations to separate and recover the propionic acid. In one embodiment the distillation of organic acids comprises a first distillation to obtain an acetic acid rich distillate and a propionic acid rich bottom (crude propionic acid stream), which is then subjected to a second distillation to obtain pure or substantially pure propionic acid. "Substantially pure" as used herein refers to purified propionic acid having minor amounts of impurities which may be still present after the distillation.

In one embodiment the distillation is vacuum distillation. In one embodiment the vacuum distillation is vacuum batch distillation. In another embodiment the vacuum distillation is continuous vacuum distillation. In the distillation different acids may be separated and recovered as different fractions, such as acetic acid, propionic acid and butyric acid.

In one embodiment there is one acid distillation. In another embodiment there are two acid distillations. In one specific embodiment the method is carried out without any acid distillations at the end. In some embodiments the method as a whole consists of any combinations of the embodiments described herein, i.e. there are no additional steps between the mentioned steps in the method procedure.

FIG. 1 illustrates one possible schematic layout for a suitable set-up for separating and subsequently recovering propionic, acid acetic acid and succinic acid from a dilute glycerol containing aqueous mixtures thereof.

In the exemplary setup of FIG. 1, dilute aqueous mixture 101 comprising glycerol and propionate is acidified with sulfuric acid 102 after which it is fed into an extraction unit 103, preferably continuously operating counter-current extraction column, together with extractant 104. The extractant contains fresh heavy extractant 122, recycled heavy extractant 121, fresh co-solvent 124 and recycled co-solvent 114. Continuous phase in the extraction may be either aqueous phase or organic phase. In case aqueous is the continuous phase, the organic phase is the dispersed phase and vice versa.

Formed extract 105 containing extractant, propionic acid, acetic acid, succinic acid, some water, co-extracted glycerol and impurities such as for example $C_4$-$C_6$ monoacids and 1-propanol, is directed to solvent distillation unit 107 where the mixture of co-solvent and water are distilled.

The raffinate 106 containing essentially water, glycerol and inorganic salts is drawn from the bottom of the extraction unit 103 and directed to further treatment.

The bottom stream 108 from solvent distillation 107 containing heavy reactive extractant, propionic acid, acetic acid, succinic acid and other co-extracted organic compounds is directed to vacuum evaporation unit 110.

The distillate 109 is drawn from the upper part of the distillation unit 107 and is fed to the decanter 111 wherein the phases are separated, and the organic phase 114 is fed to extractant preparation tank 113. The aqueous phase 115 from decanter 111 is fed back to extraction unit 103.

The extractant and succinic acid rich bottom stream 116 from vacuum evaporation 110 is directed to alkaline washing unit 112, where succinic acid and other heavy acidic components are washed with aqueous sodium hydroxide 117 and water 118 and separated from heavy extractant as purge streams 119 and 120 which are directed to further treatment. Washed heavy extractant 121 is directed into extractant preparation tank 113.

The propionic acid rich stream 123 from vacuum evaporator 110 is fed in this embodiment to a batch vacuum distillation unit 126, where acetic acid and light side product rich fractions 129 and 130 are first distilled, after which propionic acid is fractionated as pure product 131. Volatile organic acids heavier than propionic acid such as butyric acid and valeric acid are distilled as final cut 132. Propionic acid-containing intermediate fractions are recycled back to next distillation batch. Distillation residue stream 125 is directed to further treatment.

The fermentation process may utilize a bioreactor, such as a bioreactor column containing cells of the fermenting microorganism. The bioreactor as used herein refers to any suitable container, vessel or column which may be used for cultivation of microbial cells, such as for fermentation. Generally the bioreactor may be called a bioreactor column.

In one embodiment the fermentation is extractive fermentation which is carried out in situ by feeding the extracting agent directly into the bioreactor. In one embodiment the fermentation is ex situ fermentation wherein the fermentation and the extraction are carried out in separate units.

In one embodiment the fermentation prior to purifying and recovering is carried out in a bioreactor column containing cells of a fermenting microorganism attached to a surface of an immobilizing matrix, which is placed inside the column. Several immobilizing matrices are generally known in the art.

In one example the immobilizing matrix contains a first supporting material comprising a layer of sheet-like porous material, and a second cell-retaining material deposited onto the first supporting material, wherein the layers of the first supporting material and the second cell-retaining material are arranged into a rolled or folded structure allowing a sufficient flow of cell suspension medium through the immobilizing matrix. The first supporting material and the second cell-retaining material are different and separate materials, not for example a copolymer of two materials.

The immobilizing matrix allows sufficient flow of the cultivation medium through the matrix without any channeling problems. Channeling occurs usually in packed columns when the flow through the matrix is not uniform but it forms channels at certain areas of the matrix. The first and second materials are arranged to a folded structure, such as a spun or a rolled structure, which allows the flow through the structure. Usually the flow direction is axial to the rolling or folding of the matrix.

In one example the acid-producing cells, for example *Propionibacterium acidipropionicii* for propionic acid production, are at first cultivated in a continuous-flow stirred tank (CSTR) bioreactor until exponential growth phase is reached. At this stage the cells are transferred to a column reactor containing optimized immobilization matrix. This column filling allows sufficient flow through the matrix without channeling problems. Cells attach to the column filling due to the flow from the CSTR bioreactor through the column filling material and back to the CSTR reactor. The flow can be either 1 or 2-way, up or downwards or both ways. Cell loading can optionally be performed with pressurized flow in order to increase cell content and speed up the cell attachment. The loading phase can be continued until the CSTR bioreactor is empty of cells and the column filling has saturated from cells. At this point the column is detached from the CSTR bioreactor and connected to substrate feeding and product tanks to commence continuous production

EXAMPLES

Example 1

Extraction

Aqueous solution from fermentation (28.28 kg) was acidified with 96% sulfuric acid (0.49 kg), pH was decreased from 5.8 to 3.5. This solution was fed to the top part of agitated bench scale Kühni extraction column at the rate of 4.00 kg/h, where it was extracted in a counter-current mode with tri-octyl/decyl amine (Alamine 336)—cyclohexane (53:47 w/w) fed at the rate of 1.13 kg/h to the lower part of the column. Mass ratio of aqueous to organic feed was 3.53. The diameter of the extraction column was 55 mm and effective height of the column was 1.75 m with 50 mixing chambers each equipped with turbine impeller. The column had a settling zone in the top and bottom part. Organic phase was dispersed into the continuous aqueous phase at the agitation rate of 250 rpm. A clear liquid-liquid interface existed in the upper settling zone. Extraction temperature was 26° C. Extract was drawn from the top of the column at the rate of 1.21 g/h. Raffinate was drawn from the bottom of the extraction column at the rate of 3.92 kg/h.

Table 1 shows the main fermentation components in the material flows analyzed with HPLC and the calculated extraction yields (% extracted from the total amount) for each component.

TABLE 1

| Compound | Feed (Aqueous solution (101)) wt-% | Extract (105) wt-% | Raffinate (106) wt-% | Extraction yield (%) |
|---|---|---|---|---|
| Propionic acid | 2.47 | 6.20 | 0.85 | 76 |
| Succinic acid | 0.30 | 0.21 | 0.27 | 21 |
| Acetic acid | 0.03 | 0.06 | 0.02 | 53 |
| 1-Propanol | 0.04 | 0.03 | 0.03 | 27 |
| Glycerol | 0.43 | 0.00 | 0.45 | 0 |

Figure 2:
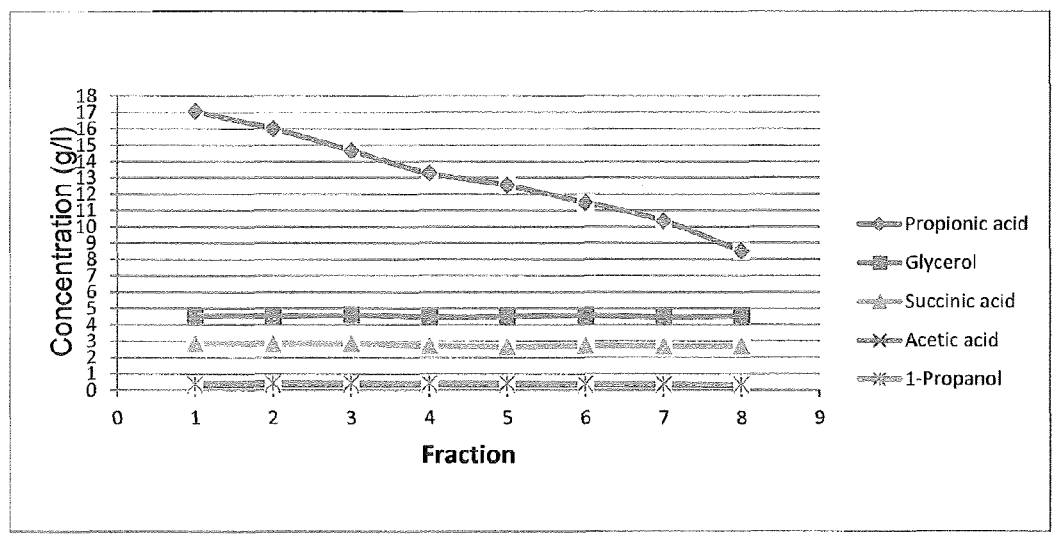
FIG. 2 shows a composition distribution in the extraction column as a concentration profile. Fractions: 1=top, 8=bottom.

FIG. 2 shows the concentration profile of the extraction column.

Example 2

Distillation

Figure 3:
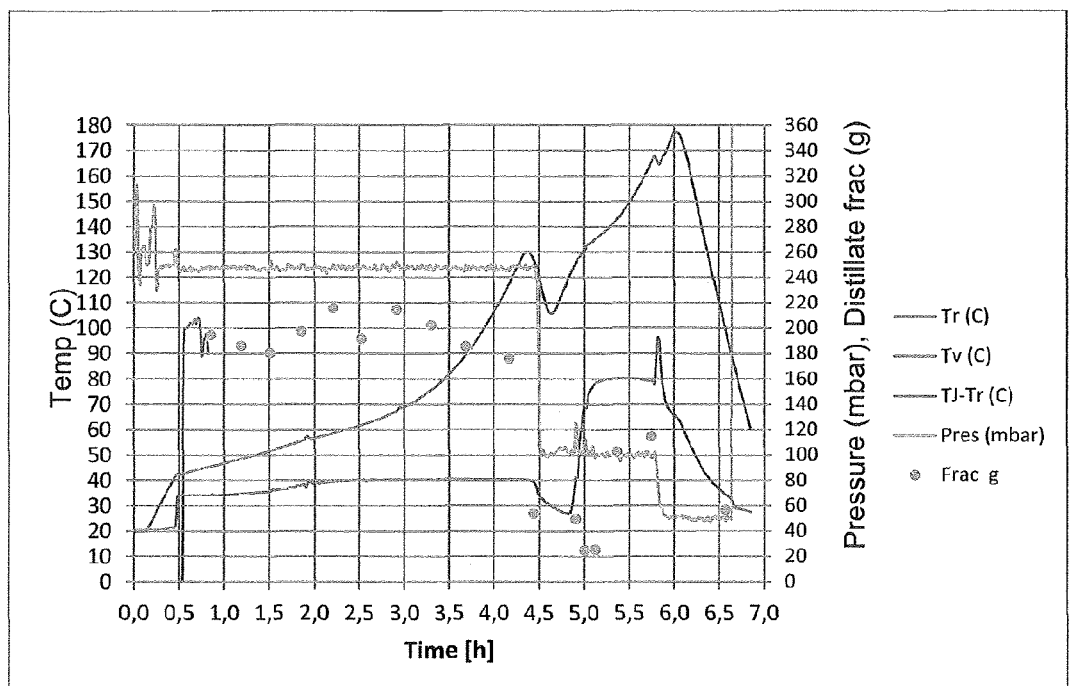
FIG. 3 shows results from recovery of propionic acid from extract (Alamine 336 with cyclohexane) in batch distillation. Tr is the reactor temperature, Tv is the temperature of distillate vapor and TJ–Tr is the temperature difference between heating medium and reactor temperature, Pres=pressure and Frac=fraction.

Cyclohexane and volatile fermentation products from the extract of Example 1 were separated from tri-octyl/decyl amine (Alamine 336), succinic acid and heavy impurities by vacuum batch distillation. The bottom temperature was gradually increased from 20° C. to 180° C. and pressure decreased from 25 kPa (250 mbar) to 5 kPa (50 mbar). 4.98 kg of extractant was fed and 2.37 kg of distillate was collected as 17 fractions. FIG. 3 shows the results from the recovery of propionic acid from extract in batch distillation Table 2 shows weights and compositions, analyzed with $^1$H-NMR, of the distillate fractions.

TABLE 2

| Distillate fraction | Distillate fraction g | Propionic acid wt-% | Acetic acid wt-% | 1-Propanol wt-% | Cyclohexane wt-% |
|---|---|---|---|---|---|
| 1 | 194.14 | 0.01 | 0.00 | 0.04 | 94.1 |
|  | (8.7) | (0.41) | (0.02) | (1.54) | (0.00) |
| 2 | 185.8 | 0.02 | 0.00 | 0.06 | 93.1 |
|  | (12.8) | (0.46) | (0.02) | (1.59) | (0.00) |
| 3 | 180.11 | 0.02 | 0.00 | 0.05 | 95.4 |
|  | (8.3) | (0.61) | (0.04) | (1.95) | (0.00) |
| 4 | 197.26 | 0.02 | 0.00 | 0.04 | 95.6 |
|  | (8.6) | (0.96) | (0.08) | (1.80) | (0.00) |
| 5 | 215.36 | 0.28 | 0.00 | 0.01 | 98.2 |
|  | (3.3) | (1.85) | (0.26) | (1.18) | (0.01) |
| 6 | 191.43 | 0.58 | 0.00 | 0.00 | 98.9 |
|  | (1.0) | (1.80) | (0.70) | (1.28) | (0.01) |
| 7 | 214.34 | 0.30 | 0.00 | 0.00 | 99.7 |
| 8 | 202.03 | 0.49 | 0.00 | 0.00 | 99.5 |
| 9 | 185.38 | 0.85 | 0.53 | 0.00 | 98.6 |
| 10 | 175.84 | 0.51 | 0.09 | 0.00 | 99.4 |
| 11 | 53.55 | 1.04 | 0.31 | 0.00 | 98.6 |
| 12 | 49.35 | 6.95 | 0.63 | 0.01 | 87.9 |
|  | (0.8) | (9.92) | (4.22) | (0.22) | (0.17) |
| 13 | 24.48 | 48.4 | 2.40 | 0.00 | 35.4 |
|  | (2.1) | (10.74) | (3.76) | (0.00) | (0.20) |
| 14 | 25.06 | 83.2 | 1.34 | 0.00 | 10.2 |
| 15 | 102.45 | 94.2 | 0.79 | 0.00 | 1.07 |
| 16 | 114.36 | 97.6 | 0.16 | 0.00 | 0.00 |
| 17 | 56.67 | 89.9 | 0.00 | 0.00 | 0.00 |

Fractions 1-6 and 12-13 contained a small amount of separate aqueous phase. The first figures are for the total sample, the figures in parenthesis for the aqueous phase.

Fractions 14-17 were obtained at bottom temperature of 120-180° C. and pressure of 5-10 kPa (50-100 mbar). Combining them gives raw propionic acid that can be easily purified further. They contained 91% of the amount of propionic acid that was present in the extract.

Example 3

Cyclohexane alone is useless as extractant in propionic acid fermentation. Amine extractants of this invention are fully regenerable.

Cell-free, acidified fermentation solution (pH 3.5, acidified with sulfuric acid) was shaken with an extractant in a separation funnel. Before extraction, the fermentation solution contained 2.40 wt-% propionic acid, 0.27 wt-% succinic acid, 0.12 wt % glycerol and 0.04 wt-% acetic acid. Cyclohexane, fresh Alamine 336 [1]—cyclohexane (53:47 w/w) and recycled. Alamine 336 [2]—cyclohexane (53:47 w/w) were used as extractants, o/w=0.25 [3], 22° C.; HPLC analyses after full separation of the phases. The results are shown in Table 3.

[1] tri(octyl/decyl amine), Cognis
[2] Recycled Alamine 336—cyclohexane was prepared from the distillation bottom of Example 2. The distillation bottom was mixed with dilute NaOH solution (final pH 7.7), the phases were let to separate and the upper phase was washed with water. The washed upper phase was separated and mixed with fresh cyclohexane.
[3] o/w is the ratio of extractant/feed (g/g)

TABLE 3

| Compound | Extraction yield with cyclohexane % | Extraction yield with fresh Alamine 336 + cyclohexane % | Extraction yield with recycled Alamine 336 + cyclohexane % |
|---|---|---|---|
| Propionic acid | 2 | 45 | 45 |
| Succinic acid | 0 | 14 | 16 |
| Acetic acid | 4 | 16 | 16 |
| Glycerol | 0 | 0 | 0 |

Examples 4-6

Three levels of cyclohexane co-solvent were used in amine extraction. The amounts of amine and feed solution were kept constant. Increasing the amount of co-solvent increased extraction selectivity to propionic acid.

Example 4

Low Cyclohexane

Cell-free, acidified fermentation solution (pH 3.5, acidified with sulfuric acid) was shaken with an extractant in a separation funnel. Alamine 336—cyclohexane (81:19 w/w) was used as the extractant, o/w=0.20, 22° C.; HPLC analyses after full separation of the phases. The results are shown in Table 4.

TABLE 4

| Compound | Acidified fermentation solution wt-% | Extract wt-% | Raffinate wt-% | Extraction yield (%) |
|---|---|---|---|---|
| Propionic acid | 2.85 | 7.36 | 1.38 | 53 |
| Succinic acid | 0.25 | 0.34 | 0.19 | 28 |
| Acetic acid | 0.03 | 0.03 | 0.03 | 17 |
| Glycerol | 0.07 | 0.04 | 0.06 | 13 |

Example 5

Medium Cyclohexane

Cell-free, acidified fermentation solution (pH 3.5, acidified with sulfuric acid) was shaken with an extractant in a separation funnel. Alamine 336—cyclohexane (51:49 w/w) was used as the extractant, o/w=0.32, 22° C.; HPLC analyses after full separation of the phases. The results are shown in Table 5.

TABLE 5

| Compound | Acidified fermentation solution wt-% | Extract wt-% | Raffinate wt-% | Extraction yield (%) |
|---|---|---|---|---|
| Propionic acid | 2.85 | 4.60 | 1.41 | 52 |
| Succinic acid | 0.25 | 0.11 | 0.22 | 15 |
| Acetic acid | 0.03 | 0.01 | 0.03 | 15 |
| Glycerol | 0.07 | 0.03 | 0.06 | 15 |

Example 6

High Cyclohexane

Cell-free, acidified fermentation solution (pH 3.5, acidified with sulfuric acid) was shaken with an extractant in a separation funnel. Alamine 336—cyclohexane (31:69 w/w) was used as the extractant, o/w=0.53, 22° C.; HPLC analyses after full separation of the phases. The results are shown in Table 6.

TABLE 6

| Compound | Acidified fermentation solution wt-% | Extract wt-% | Raffinate wt-% | Extraction yield (%) |
|---|---|---|---|---|
| Propionic acid | 2.87 | 2.71 | 1.46 | 50 |
| Succinic acid | 0.25 | 0.03 | 0.24 | 5 |
| Acetic acid | 0.03 | 0.01 | 0.03 | 9 |
| Glycerol | 0.07 | 0.01 | 0.06 | 11 |

Example 7

Structure of the Amine Extractant Affects Propionic Acid Recovery 5 wt-% propionic acid solution in water was adjusted to pH 3.5 with 5 M NaOH. The solution was extracted by shaking with amine-cyclohexane mixtures (67:33 w/w). The ratio o/w was varied so that amine (mol)/acid (mol)=0.733-1.10. The amines used were tri(octyl/decyl)amine (Alamine 336) and trihexylamine. After separation of phases the raffinate was analyzed with HPLC. The results are shown in Table 7.

TABLE 7

| Amine/ propionic acid (mol/mol) | Extraction yield with tri(octyl/decyl amine) + cyclohexane % | Extraction yield with trihexylamine + cyclohexane % |
|---|---|---|
| 1.10 | 59.2 | 60.5 |
| 0.943 | 57.8 | 60.4 |
| 0.825 | 55.9 | 60.8 |
| 0.733 | 54.9 | 60.9 |

Example 8

Increasing the Amount of Extraction Steps Increases the Extraction Selectivity to Propionic Acid Cell-free, acidified fermentation solution (pH 3.5, acidified with sulfuric acid) was shaken four times with fresh extractant in a separation funnel. Trihexylamine—cyclohexane (67:33 w/w) was used as the extractant, o/w=0.16, 22° C. After each step the phases were let to separate and the raffinate was analyzed with HPLC. The results are shown in Table 8.

TABLE 8

| Compound | Acidified fermentation solution wt-% | Raffinate after 1. extraction wt-% | Raffinate after 2. extraction wt-% | Raffinate after 3. extraction wt-% | Raffinate after 4. extraction wt-% | Extraction yield % |
|---|---|---|---|---|---|---|
| Propionic acid | 2.77 | 1.42 | 1.08 | 0.89 | 0.77 | 72 |
| Succinic acid | 0.25 | 0.15 | 0.15 | 0.15 | 0.15 | 39 |
| Acetic acid | 0.05 | 0.04 | 0.04 | 0.04 | 0.04 | 19 |
| Glycerol | 0.06 | 0.06 | 0.07 | 0.07 | 0.07 | 0 |

The invention claimed is:
1. A method for purifying and recovering propionic acid from an aqueous mixture containing a fermentation product obtained from a fermentation process using glycerol as substrate, wherein the method comprises subjecting the aqueous mixture to an extraction with an extracting agent to obtain an extract containing the extracting agent and organic acids, and a raffinate containing water and any unreacted glycerol, and subjecting the extract to a vacuum evaporation to separate propionic acid-containing organic acids from the extractant.

2. The method according to claim 1, comprising the step of acidifying the aqueous mixture to a pH of below 4.5.

3. The method according to claim 1, wherein the extracting agent further comprises a diluent.

4. The method according to claim 3, comprising the step of acidifying the aqueous mixture to a pH of below 4.5.

5. The method according to claim 1, which further comprises subjecting the organic acids from the vacuum evaporation to at least one distillation to separate and recover the propionic acid.

6. The method according to claim 1, which further comprises subjecting the extract from the extraction to co-solvent distillation.

7. The method according to claim 1, which comprises recycling the extractant from the vacuum evaporation back to the extraction.

8. The method according to claim 1, wherein the extraction is a countercurrent extraction.

9. The method according to claim 1, which comprises recycling the glycerol-containing raffinate from the extraction back to the fermentation process.

10. The method according to claim 1, wherein the extracting agent is selected from trihexyl amine, trioctyl amine, triisooctylamine, tri-(octyl-decyl)amine, tridodecylamine and mixtures thereof.

11. The method according to claim 1, wherein the extracting agent comprises tri-(octyl-decyl)amine.

12. The method according to claim 1, wherein the extracting agent further comprises an extractant selected from n-hexane, n-heptane, cyclohexane, benzene, toluene and mixtures thereof.

13. The method according to claim 1, wherein the extracting agent comprises tri-octyl/decyl amine with cyclohexane.

14. The method according to claim 13, wherein the extracting agent comprises about 45% (w/w) cyclohexane.

15. The method according to claim 1, wherein the mass ratio of the dilute aqueous mixture to the extracting agent in the feed is in the range of 0.25-4.0.

16. The method according to claim 1, wherein the extraction is carried out at a temperature in the range of 10-80° C. and at a pressure of at most 500 kPa absolute.

17. The method according to claim 5, wherein the co-solvent distillation is carried out at a temperature in the range of 30-110° C.

18. The method according to claim 1, wherein the vacuum evaporation is carried out at a temperature in the range of 30-200° C.

19. The method according to claim 1, wherein the vacuum evaporation is carried out at a pressure below 25 kPa absolute.

20. The method according to claim 4, wherein the distillation of organic acids comprises a first distillation to obtain a propionic acid rich stream, which is then subjected to a second distillation to obtain pure propionic acid.

21. The method according to claim 1, wherein the fermentation process is an extractive fermentation process.

22. The method according to claim 1, wherein the fermentation process and the extraction are carried out separately.

23. The method according to claim 1, wherein the mass ratio of the dilute aqueous mixture to the extracting agent in the feed is in the range of 0.75-2.0.

* * * * *